(12) United States Patent
Hu et al.

(10) Patent No.: US 6,680,067 B2
(45) Date of Patent: Jan. 20, 2004

(54) CONTROLLED-RELEASE PHARMACEUTICAL PREPARATION CONTAINING NALBUPHINE AND A PROCESS FOR PREPARING THE SAME

(75) Inventors: Oliver Yoa-Pu Hu, 2F, No.81, Alley 5, Lane 24, Sec. 3, Ting-Chou Road, Taipei (TW); Cheng-Huei Hsiong, Taipei (TW)

(73) Assignee: Oliver Yoa-Pu Hu, Taipei (TW)

( * ) Notice: Subject to any disclaimer, the term of this patent is extended or adjusted under 35 U.S.C. 154(b) by 59 days.

(21) Appl. No.: 09/991,608

(22) Filed: Nov. 26, 2001

(65) Prior Publication Data

US 2003/0113372 A1 Jun. 19, 2003

(51) Int. Cl.[7] ............................. A61F 2/02; A61F 13/02; A61K 9/70; A61K 9/50

(52) U.S. Cl. ........................ 424/423; 424/449; 424/497

(58) Field of Search ................................ 424/423, 449, 424/497

(56) References Cited

U.S. PATENT DOCUMENTS

| | | | |
|---|---|---|---|
| 5,750,534 A | 5/1998 | Yoa-Pu et al. | |
| 6,197,344 B1 * | 3/2001 | Chang et al. | 424/489 |
| 6,225,321 B1 | 5/2001 | Hu et al. | |

OTHER PUBLICATIONS

S. Sabnis; Factors Influencing the Bioavailability of Peroral Formulations of Drugs for Dogs; Veterinary Research Communications, 1999, P 425–447, vol. 23; Kluwer Academic Publishers, Netherlands.

J. Zuidema et al.; Release and absorption rates of intramuscularly and subcutaneously injected pharmaceuticals (II); International Journal of Pharmaceutics, 1994, P 189–207, vol. 105; Elsevier Science B.V.

M.K. Al–Hindawi et al.; Influence of solvent on the availability of testosterone propionate from oily, intramuscular injections in the rat; J. Pharm. Pharmacol, 1987, P 90–95, vol. 39.

Jane Croft Harrelson et al.; Species variation in the disposition of nalbuphine and its acetylsalicylate ester analogue; Xenobiotica, 1988, P 1239–1247, vol. 18, No. 11.

* cited by examiner

*Primary Examiner*—Carlos Azpuru
(74) *Attorney, Agent, or Firm*—Fei-Fei Chao; Venable LLP

(57) ABSTRACT

A controlled-release pharmaceutical preparation containing an oil suspension which comprises an analgesic and an injectable oil. The analgesic is either a nalbuphine free base or a pharmaceutical salt of nalbuphine such as nalbuphine HCl. The injectable oil is preferably sesame oil. The oil suspension contains microparticles in the size range of 1 to 100 μm, preferably less than 50 μm, which is produced by treating the analgesic and injectable oil in an ultra high energy mixing equipment. The controlled-release preparation permits nalbuphine free base or nalbuphine HCl to have a longer duration of action in relieving pain, and allows the administration of lower doses. A process for preparing the injectable oil suspension is also disclosed.

19 Claims, 8 Drawing Sheets

(I) Buprenorphine (II) Nalbuphine (III) Butorphanol (I) Buprenorphine (II) Nalbuphine (III) Butorphanol

CONTROLLED-RELEASE PHARMACEUTICAL PREPARATION CONTAINING NALBUPHINE AND A PROCESS FOR PREPARING THE SAME

FIELD OF THE INVENTION

This invention relates to a controlled-release pharmaceutical preparation which includes an analgesic which is in admixture with an injectable oil, and optionally containing a pharmaceutically acceptable excipient. The preferred analgesic is nalbuphine free base or a pharmaceutically acceptable salt of nalbuphine (preferably nalbuphine-HCl). The preferred injectable oil includes sesame oil, ethyl ester of peanut oil, soybean oil, and any combinations thereof. The pharmaceutical composition is further characterized by its containing of microparticles with size less than 100 μm. The controlled-release pharmaceutical preparation exerts a long-acting analgesic effect when being administered intramuscularly, subcutaneously, intracerebroventricularly or percutaneously. A process for preparing the controlled-release pharmaceutical preparation is also disclosed herein.

BACKGROUND OF THE INVENTION

An ideal analgesic should exhibit short onset time, should be potent and long-acting, should cause no addiction, no inhibition of the cardiac or cardiovascular system and no respiratory inhibition, and should have rare other adverse effects.

Local anesthetics like xylocaine or bupivacaine are effective to relieve pain only within limited areas. In addition, local anesthetics are short-acting and exhibit duration of action normally no more than 6 hours even when being given intracerebroventricularly. Therefore, local anesthetics are not satisfactory for the relief of acute and severe pain caused by cardiac, pulmonary, abdominal, osteopathic or obstetrical surgery, severe burn injury and terminal stage of cancer.

Non-narcotic analgesics, such as aspirin and acetaminophen, relieve pain of only low intensity, such as pain due to headache or toothache, but they do not help in the case of severe pain. For the pain of high intensity and widespread in origin, narcotic analgesics have been particularly referred to in literature, amongst which morphine, meperidine and fentanyl are reported to interact with specific receptors (i.e. mu receptor) in the CNS and exhibit potent analgesic activity. However, all the narcotic analgesics exhibit common disadvantages such as addiction and respiratory inhibition (Hayes, A. G. et al., Br. J. Pharmacol., Vol.79, pp.731, 1983). The most unwanted problem associated with the long-term use of narcotic analgesics is the incidence of addiction. In addition, it is not unusual that narcotic analgesics induce severe respiratory depression and even death in patients with poor respiratory function or post cardiac or chest surgery. Moreover, narcotic analgesics exhibit a relatively short duration of action and, therefore, under normal conditions, a dosing interval of 3–5 hours is required so as to maintain of the intended analgesic effect thereof. Even when the agent is directly administered to the spinal marrow, the duration of action would not last for a period of more than 48 hours. In addition, if a larger dose of the agent, e.g. morphine of 0.5–1.0 mg/dose, is used to provide a prolonged analgesic effect, fatal respiratory depression is likely to occur (Baxter. A. D. et al., Can. J. Anesth., Vol. 36. pp.503, 1989).

Recently, there have been developed a new class of opioids called narcotic agonist-antagonist analgesics, the representatives of which include nalbuphine, buprenorphine and butorphanolm, the chemical structures of which are shown in FIG. 1. These analgesics are reported to exhibit a dual action of agonism and antagonism on opioids-receptors (Schmidt, W. F. et al., Drug Alcohol Depend., Vol. 14, pp.339, 1985). For instance, nalbuphine is an antagonist for the mu receptor and an agonist for the kappa receptor. After a continuous administration period of six months, nalbuphine appears to cause no significant addiction while resulting in only slight respiratory inhibition. Due to these observed pharmacological properties, the adverse effects normally associated with narcotic analgesics have been greatly improved by this new class of narcotic analgesics, which decrease the incidence of addiction and diminish the inhibitory effect on the respiratory system.

The analgesic potency of this new class of narcotic analgesics have been investigated and compared with the more traditional class of narcotic analgesics which elicit addiction. It has been found that the doses needed to elicit the same analgesic effect by morphine, buprenorphine, nalbuphine and butorphanol are 10 mg, 0.3 mg, 10 mg and 2 mg, respectively (Shafer, S. L. et al., Anesthesiology, Vol. 74, pp.53, 1991). According to the report of Schmidt, W. K. et al. (1985), supra, nalbuphine is most widely used amongst this new class of narcotic analgesics and it exhibits excellent therapeutic efficacy. In clinical use, nalbuphine exhibits only slight respiratory inhibition and is therefore safer than the traditional narcotic analgesics which elicit addiction.

Nalbuphine has been found to be effective in control of severe and deep pain caused by cardiac, pulmonary, abdominal, osteopathic or obstetrical surgery, severe burn injury and the terminal stage of cancer via various administration routes, such as intramuscular, intravenous and intrathecal administrations (Schmidt, W. K. et al. (1985), supra). Wang, J. J. et al. (Ma. Tsui. Hsueh. Tsa. Chi., Vol. 23, pp.3, 1985) have reported that the effect of nalbuphine can only last for 3–5 hours after intravenous administration and 6–8 hours by intrathecal injection, respectively. However, severe pain usually cannot be relieved in such short periods of time. Therefore, the clinical use of nalbuphine is still not satisfactory due to its short duration of action.

An improvement that effectively extends the duration of action of a target drug is a significant advance in the field of medicine, as such improvement is considered to enable the more economical utilization of medical resources. To achieve this purpose, a widely employed approach is to modify the dosage form of a drug that is normally eliminated rapidly in vivo, so that the duration of action of the drug is extended.

In order to control or prolong the duration of action of a target drug during clinical use, various pharmaceutical preparations have been developed. For example, the target drug may be coated with cyclodextrin or acrylic polymers, or manufactured in the form of microcapsules or microparticles, so that release of the drug is controlled or delayed. However, pharmaceutical preparations in such forms do not always provide effective controlled release of active component(s) therefrom.

It has been found that for narcotic analgesics that may cause addiction, it is possible to decrease the release rate and the side effects thereof via subcutaneous administration. The subcutaneous area has less blood flow and more adipose tissue than other parts of the human or animal body, so that when a lipophilic drug is subcutaneously administered into the subcutaneous areas, the release thereof slows down.

With respect to the intracerebroventricular or spinal cord administration, the increased duration of action and the decreased side effects of narcotic analgesics, such as morphine, fentanyl, buprenorphine and nalbuphine, have been investigated by Rutter, D. V. et al. (*Br. J. Anesth.*, Vol. 53, pp. 915, 1981). In addition to the administration routes described above, the percutaneous administration of narcotic analgesics is also considered to be promising. Hill, H. F. et al. (*Eur., J. Pharmacol.*, Vol. 119, pp.23, 1985) have proposed a dosage form of fentanyl for percutaneous administration having a safety range of 0.6–3 $\mu$g/ml, which is the same as that of narcotic analgesics acting on the mu-receptor.

In U.S. Pat. No. 4,673,679 issued to Bruce et al. on Jun. 16, 1987, it is stated that morphine, fentanyl, buprenorphine and nalbuphine derivatives in the sublingual, buccal or nasal dosage form exhibit enhanced bioavailability. However, Bruce et al. did not investigate the analgesic action and the long-acting effect of nalbuphine free base. No injectable dosage form of nalbuphine free base suitable for therapeutic use has been described.

Accordingly, there still exists a need for a new dosage form of nalbuphine free base or nalbuphine HCl which effectively extends the duration of action of nalbuphine free base in vivo.

SUMMARY OF THE INVENTION

Therefore, it is an object of this invention to provide a controlled-release pharmaceutical preparation which is an oil suspension comprising an analgesic which is a nalbuphine free base or a pharmaceutically acceptable salt of nalbuphine, which is in admixture with an injectable oil, so that the duration of action of the analgesic in relieving pain is prolonged in vivo. The pharmaceutically acceptable salt of nalbuphine includes acid addition salt of nalbuphine or an alkali or alkaline earth metal salt thereof. The most favorable pharmaceutical acceptable salt of nalbuphine is nalbuphine HCl. The preferred injectable oil includes sesame oil, ethyl ester of peanut oil, soybean oil, and any combination of the oil. Sesame oil is the most favorable injectable oil. Optionally, a pharmaceutically acceptable excipient, such as aluminum stearate, chlorobutanol hydrate, methyl paraben, propyl paraben, and any combinations thereof, can be added to the oil suspension.

The controlled-release pharmaceutical preparation of the present invention is further characterized by its formation of microparticles in the oil suspension with size less than 100 $\mu$m, most preferably less than 50 $\mu$m. The microparticles of the oil suspension is formed by mixing the analgesic and the injectable oil in an ultra high energy mixing equipment, such as MicroFludizer high pressure homogenizer, Emulsiflex, and Manton-Gaulin, preferably under a pressure of 10,000 to 30,000 psi, and most favorably at about 14,000 psi. The preferred length of time to operate the ultra high energy mixing equipment is about 10 to 75 minutes.

Also preferably, the controlled-release pharmaceutical preparation of the present invention is administered via an intramuscular, subcutaneous, intracerebroventricular or percutaneous route, or for direct injection into the spinal marrow. The most preferred route is through intramuscular injection.

It is contemplated that the injectable oil suspension of this invention possesses the desired properties for an analgesic as discussed above, such as being long acting, fast acting (short onset time), and nonaddictive, and not causing other undesirable side effects such as inhibition of the cardiac or cardiovascular system, respiratory system, etc.

It is another object of this invention to provide a process for making a controlled-release pharmaceutical preparation which includes the steps of: (1) mixing the analgesic with the injectable oil to form the oil suspension, and (2) treating the oil suspension with an ultra high energy mixing equipment to form microparticles with a particle size less than 100 $\mu$m, preferably no more than 50 $\mu$m in size. The preferred analgesic is nalbuphine free base or a pharmaceutically acceptable salt of nalbuphine. The preferred pharmaceutically acceptable salt of nalbuphine includes acid addition salt of nalbuphine or an alkali or alkaline earth metal salt thereof. The most favorable pharmaceutical acceptable salt of nalbuphine is nalbuphine HCl. The preferred injectable oil includes sesame oil, ethyl ester of peanut oil, soybean oil, and any combinations thereof.

Preferably, the injectable oil is pre-heated to about 45° C. before mixing with the analgesic. After mixed or homogeneously suspended with the analgesic, the analgesic-injectable oil mixture is cooled to room temperature, and then treated with an ultra high energy mixing equipment. Examples of the ultra high energy mixing equipment include, but are not limited to, MICROFLUIDIZER high pressure homogenizer (Model 110-S or 110-Y, Microfluidics Corp., Newton, Mass.), EMULSIFLEX (Avestin Inc., Ottawa, Ontario, Canada), or Manton-GAULIN (APV Gaulin Rannie, St. Paul, Minn.). The preferred ultra high energy mixing equipment is MICROFLUIDIZER high pressure homogenizer M110-Y.

Also preferably, the analgesic can be pre-mixed with a pharmaceutically acceptable excipient, such as aluminum stearate, chlorobutanol hydrate, methyl paraben, propyl paraben, and any combinations thereof.

This invention provides an injectable oil suspension containing nalbuphine free base or nalbuphine HCl, which exhibits a longer duration of action when being administered intramuscularly or subcutaneously. The injectable oil suspension according to this invention may be used in the treatment of living subjects, preferably mammals, and in particular humans suffering severe pain.

BRIEF DESCRIPTION OF THE DRAWINGS

These and other objects and features of the present invention will become better understood with reference to the following descriptions, appended claims, and accompanying drawings of which:

DETAILED DESCRIPTION OF THE INVENTION

Figure 1:
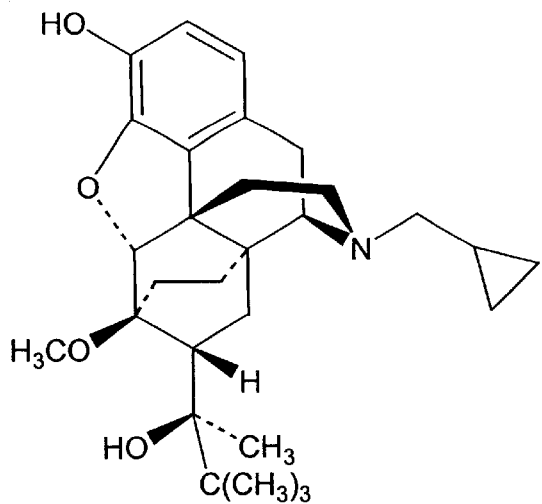
FIG. 1 shows the chemical structure of three narcotic agonist-antagonist analgesics: (I) buprenorphine, (II) nalbuphine free base, and (III) butorphanol.
Figure 1:
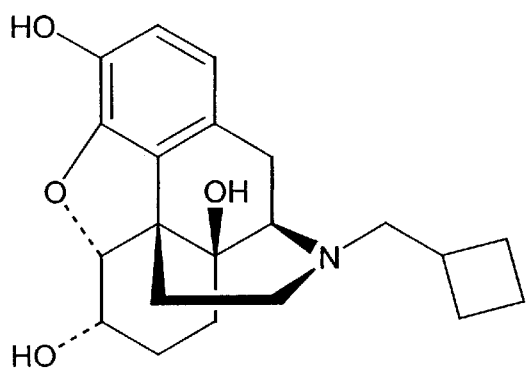
Figure 1:
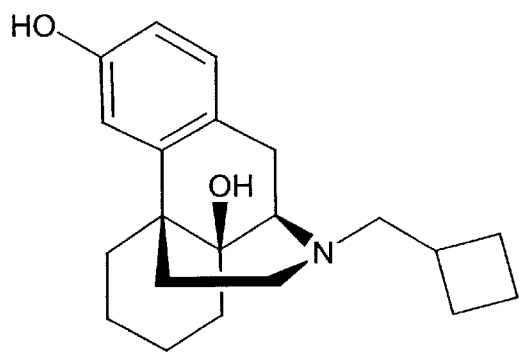

In general, to achieve the long acting therapeutic efficacy of a target drug, various dosage forms are prepared by which the target drug may be esterified and even suspended in an oil vehicle to form a suspension for parenteral administration, so that when administered to a human or animal subject, the release rate of the target drug is slowed due to the influence of factors such as increased solubility of the target drug in fat or low blood flow in the vicinity of the site of administration. In these cases, the dosing interval of the target drug may be lengthened by virtue of the prolonged duration of action thereof.

Gelders reported in *Int. Clin. Psychophacol.*, Vol. 1, page 1 (1986), and Hinko, C. N. et al. reported in *Neuropharmacology*, Vol. 27, page 475 (1998), the formation of a controlled-release dosage forms by addition of an injectable oil, such as sesame oil, soybean oil or ethyl ester of peanut oil with 5% esterification to a prodrug Haloperidol decanoate. However, due to unknown factors, rapid release of a target drug from an oil suspension sometimes occurs. For instance, the release of testosterone from the intramuscular administration of a testosterone suspension was found to be rapid (Tanaka, T., *Chem. Pharm. Bull.*, Vol. 22, pps. 1275–1284 (1974). Titulaer, H. A. C. reported the suspension of artemisinin in parenteral oil to form various dosage forms for intramuscular, intravenous, oral or rectal administration. However, the drug was released quickly from such dosage forms (*J. Pharm. Pharmacol.*, Vol. 42, pp. 810–813, 1990). Zuidema, Z. et al. reported in *International J. of Pharmaceutics* (1994), Vol. 105, pp. 189–207 that the release rate and extent of dosage forms for parenteral administration are very erratic and variable.

According to the aforementioned studies, a dosage form which contains a pharmaceutical composition suspended, dissolved or esterified in an oil vehicle does not necessarily exhibit a longer duration of therapeutic effect. In general, any attempt to suspend a target drug in an oil vehicle for the purpose of obtaining long-acting dosage forms must to take into account the physical solubility, stability, and release rate of the target drug from such vehicle.

In developing a long-acting injectable oil suspension for nalbuphine free base, a number of factors are considered to have influence upon the release rate of nalbuphine free base, for example, the blood flow in the vicinity of the injection site, the lipophilicity of the injectable oil suspension, and the particle size of microparticles suspended in the injectable oil suspension.

The present invention provides a controlled-release pharmaceutical preparation that comprises an oil suspension containing an analgesic selected from nalbuphine free base and a pharmaceutically acceptable salt of nalbuphine such as nalbuphine HCl, which is in admixture with an injectable oil, and optionally a pharmaceutically acceptable excipient. This preparation permits nalbuphine free base or nalbuphine HCl contained therein to have a longer duration of action in relieving pain.

This invention also discloses a process for preparing a controlled-release pharmaceutical preparation of an oil suspension containing nalbuphine free base or nalbuphine HCl. Generally, nalbuphine free base or nalbuphine HCl is placed into a suitable container (e.g. a glass flask), followed by addition of a pharmaceutically acceptable excipient, such as methyl paraben, propyl paraben, chlorobutanol hydrate, or aluminum stearate, or any combinations thereof.

An injectable oil which is pre-heated to 40–50° C. (preferably about 45° C.) is then added and mixed together therewith. These ingredients are homogeneously mixed to form the oil suspension. A high speed mixer, such as a Polytron homogenizer (Kinematica GmbH, Lucerne, Switerland) or Ultra Turrax (IKA-Works, Cincinnati, Ohio), operating at 3000–12,500 rpm 40–55° C. for at least 5 minutes, can be used for this purpose.

Thereafter, the oil suspension is cooled to room temperature and treated with an ultra high energy mixing equipment. Examples of the ultra high energy mixing equipment include, but are not limited to, MICROFLUIDIZER high pressure homogenizer (Model 110-S or 110-Y, Microfluidics Corp., Newton, Mass.), EMULSIFLEX (Avestin Inc., Ottawa, Ontario, Canada), or Manton-GAULIN (APV Gaulin Rannie, St. Paul, Minn.). The preferred ultra high energy mixing equipment is MICROFLUIDIZER high pressure homogenizer M110-Y. The ultra high energy mixing equipment is operating in the recycling mode at 30–60° C. and 10,000 to 30,000 psi, and preferably at about 12,500–18, 200 psi (most favorably about 14,000 psi), for 30—30 minutes. After processing, the analgesic-injectable oil mixture is passed sequentially through sterile 0.45 μm and 0.22 μm sterile filters. The sequential filtration removes any large particles and partially sterilizes the product.

The temperature for high energy mixing should be chosen relative to the bioactive agent. In other words, the temperature should be greater than or equal to the transition temperature or melting point of the bioactive agent. An upper bound should be determined by whether the temperature would cause degradation or decomposition of any components in the composition. The optimal temperature for the present invention is at room temperature.

The resulting microparticles are in the size range of between 1 and 100 μm. The use of the ultra high mixing equipment ensures small particle size with a narrow size range distribution, which is superior to conventional homogenization systems, such as using homogenizers, sonicators, mills, and shaking systems. The conventional homogenization systems provide a shearing force on the liquid components whereas the ultra high energy mixing equipment puts the components under pressure and forces them through small openings to reduce particle size. Size distribution may be measured by a Nicomp 370 Dynamic Laser Light Scattering Autocorrelator (Nicomp Particle Sizing Systems, Santa Barbara, Calif.) or similar equipment.

The controlled-release pharmaceutical preparation of the present invention could be administered via the intramuscular, subcutaneous, intracerebroventricular or percutaneous route, or directly injected into the spinal marrow. The most preferred route is intramuscular.

The injectable oil suitable for use in this invention includes, but not limited to an oil selected from sesame oil, ethyl ester of peanut oil, and soybean oil, or a combination thereof.

Pharmaceutically acceptable excipients are optional and include aluminum stearate, chlorobutanol hydrate, methyl paraben, propyl paraben, and combinations thereof. Additional pharmaceutically acceptable excipients will be known to those of skill in the art.

The following examples are given for the purpose of illustration only and are not intended to limit the scope of the present invention.

EXAMPLE 1

Oil Selection to be Used for Injection of
Nalbuphine HCl or Nalbuphine Free Base Material To select a suitable oil as the oil vehicle for the controlled-release pharmaceutical preparation of this invention, sesame oil, soybean oil and an ethyl ester of peanut oil were tested using the following dialysis test. Phosphate buffer (1.9 g monobasic potassium phosphate, 8.1 g dibasic sodium phosphate, and 4.11 g sodium chloride were dissolved in 1 L water to make an isotonic solution of pH 7.4) was used as control.

Experimental Procedures

Each experimental group consisted of 6 samples. Into a dialysis bag was placed 50 mg (0.127 mmole) of Nalbuphine hydrochloride, or 45 mg Nalbuphine free base (0.127 mmole), followed by addition of 1 ml of a selected oil or phosphate buffer. The resulting mixture was placed in a dialysis bag having a molecular weight cut-off value of 12,000–14,000 dalton. The dialysis bag was placed into a 250 ml iodine flask containing 150 ml of phosphate buffer and equipped with a magnetic stirring bar (Fargo, Taipei, ROC). Dialysis was performed at a stirring speed of 500 rpm, and the release rate of nalbuphine HCl or nalbuphine free base from each sample was measured. An UV spectrophotometer UV-160 (Shimadzu, Kyoto, Japan) was used to detect the content of nalbuphine released into the phosphate buffer surrounding the dialysis bag.

Result

Figure 2:
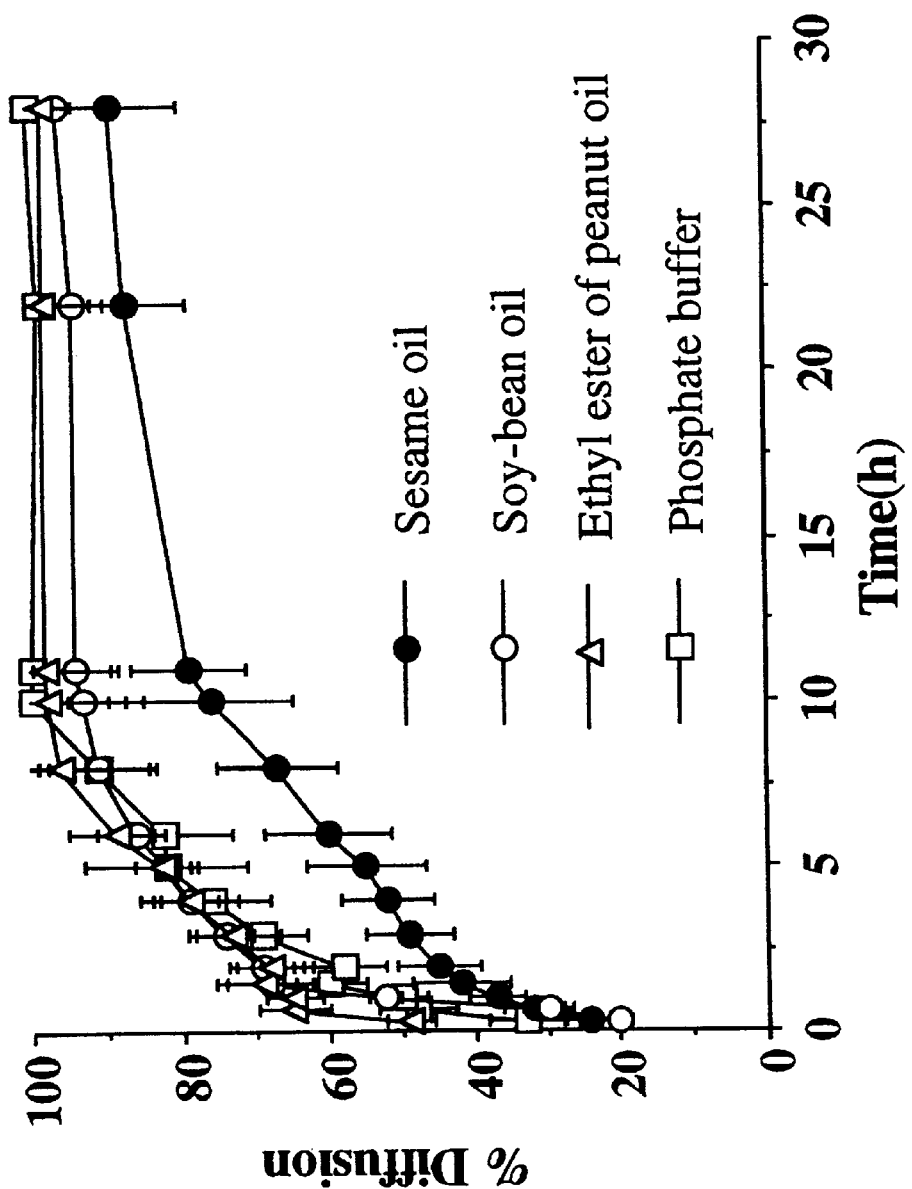
FIG. 2 shows the in vitro release profiles of nalbuphine HCl from the tested injectable oil suspensions prepared in the selected oils acting as a vehicle, in which: (●), sesame oil; (○), soybean oil; (△), ethyl ester of peanut oil; and (□), phosphate buffer as the control.
Figure 3:
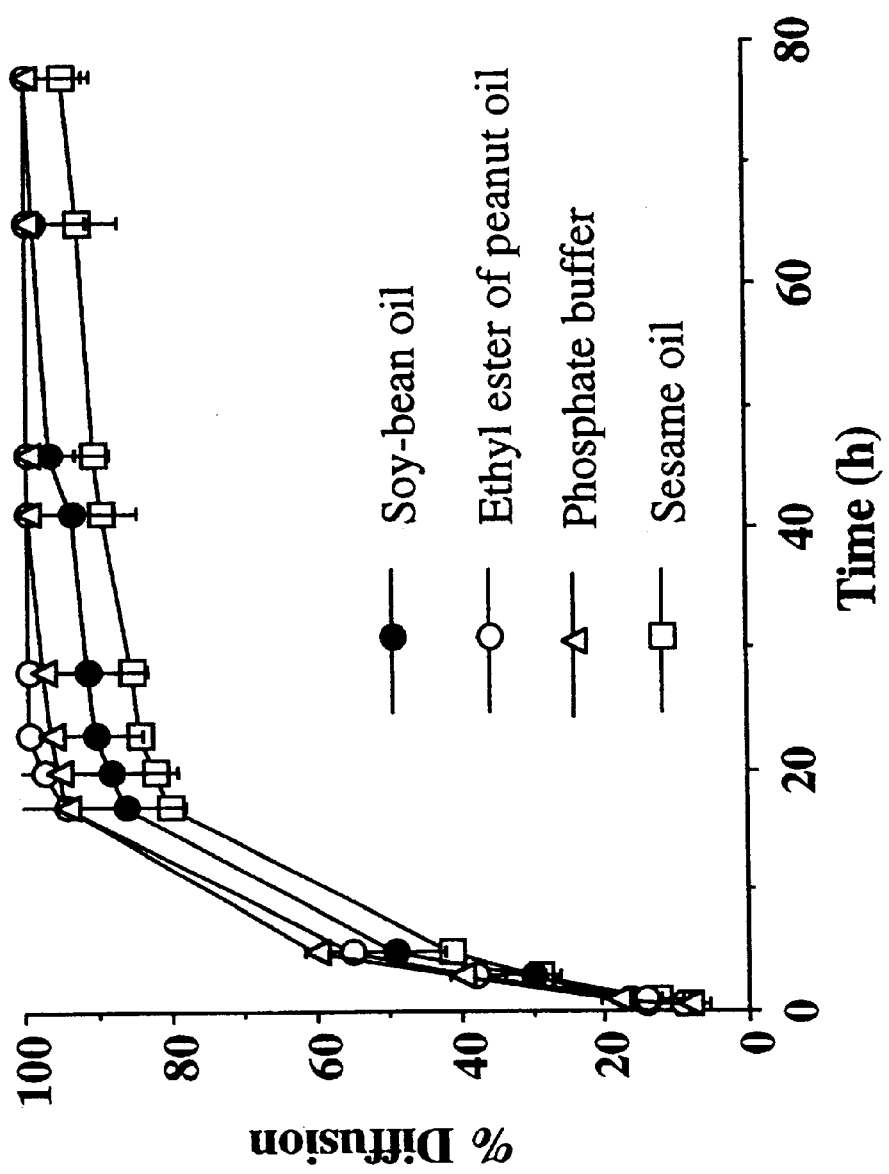
FIG. 3 shows the in vitro release profiles of nalbuphine free base from the tested injectable oil suspensions prepared in the selected oils acting as a vehicle, in which: (●), soybean oil; (□), sesame oil; (○), ethyl ester of peanut oil; and (△), phosphate buffer as the control.
Figure 4:
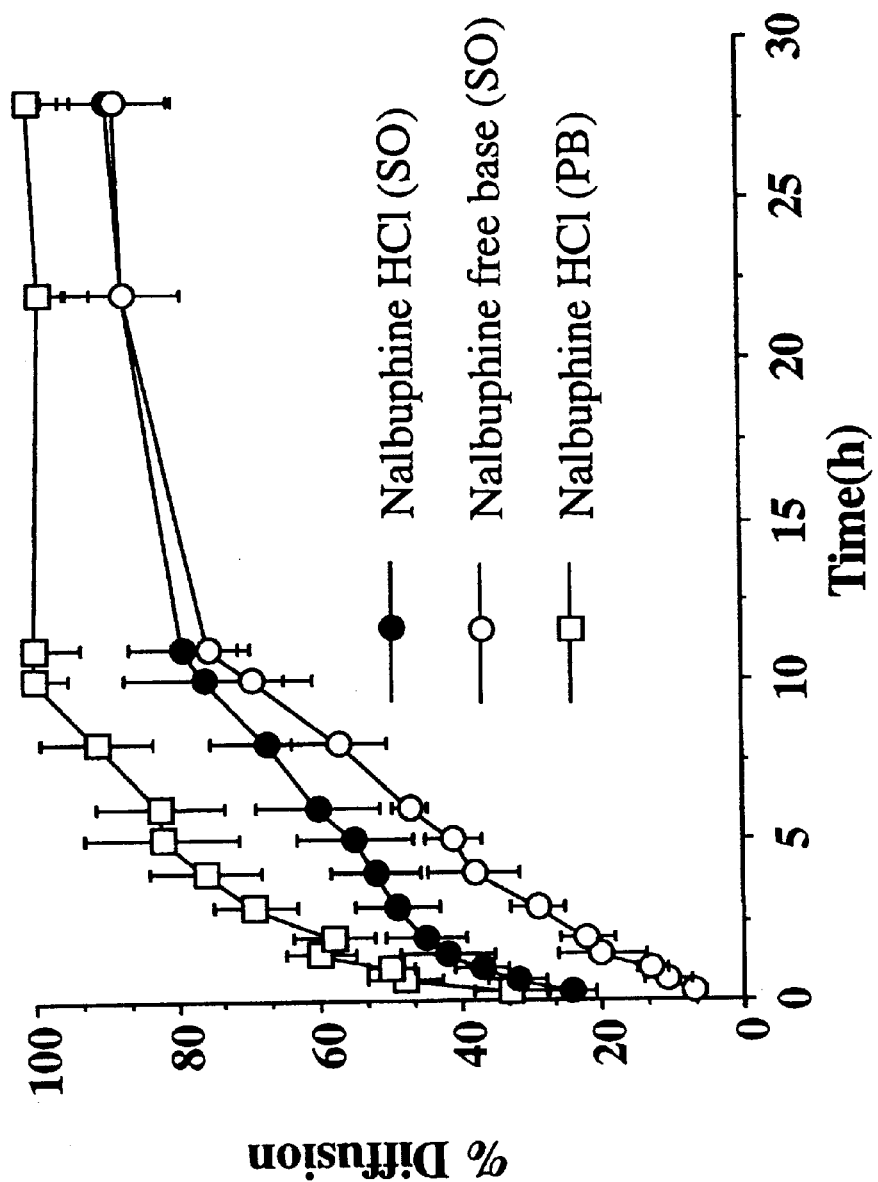
FIG. 4 shows the in vitro release profiles of nalbuphine HCl or nalbuphine free base from the tested injectable oil suspensions prepared in sesame oil, in which: (●), nalbuphine HCl in sesame oil; (○), nalbuphine free base in sesame oil; and (□), nalbuphine HCl in phosphate buffer.

FIGS. 2, 3 and 4 show the in vitro release profile of nalbuphine HCl or nalbuphine free base from each sample (prepared with the selected oil or phosphate buffer), respectively.

Referring to FIG. 2, the tested sample group prepared with sesame oil as the oil vehicle has the lowest rate ($p<0.05$) and there is no significant difference within the other three tested groups.

FIG. 3 shows that the released amount of nalbuphine free base from the sample group prepared with sesame oil was less than the sample group prepared with ethyl ester of peanut oil and the control group after a period of between 17 and 28 hours ($p<0.05$).

FIG. 4 shows the released amount of nalbuphine from preparation (A) nalbuphine HCl in sesame oil, preparation (B) nalbuphine HCl in phosphate buffer, and preparation (C) nalbuphine free base in sesame oil. After three hours, the release of nalbuphine HCl from preparation (B) is greater than that from preparation (A), and preparation (C) shows the lowest release rate.

EXAMPLE 2

Preparation of Injectable Oil Suspension

Based on the above findings, injectable oil suspensions having the formulations shown in Table 1 were prepared according to the preparative procedures summarized in Table 2. The detected physical characteristics of the injectable oil suspensions are also shown in Table 2.

1. Injectable Oil RH001 Containing Nalbuphine Free Base

Into a 1 ml flask were added 75 mg nalbuphine free base, 1.8 mg methyl paraben, 0.2 mg propyl paraben, and 2.0 mg aluminum stearate. Sesame oil pre-heated to 45° C. was then added into the flask to a total volume of 1 ml. After the above ingredients were homogeneously suspended in sesame oil with stirring, the resultant suspension was cooled to room temperature and treated with a pneumatic microfluidizer M110-Y (Microfluidics Corp., Mass., USA) under a pressure of 14,000 psi for 60 minutes, so as to decrease the particle size of the suspended microparticles.

2. Injectable Oil RH002 Containing Nalbuphine Free Base

This oil was prepared according to the above preparative procedure for Injectable oil RH001, except that 50 mg nalbuphine free base was used and a microfluidizer was used for 60 minutes to decrease the particle size of the microparticles suspended in the oil suspension.

3. Injectable Oil RH044 Containing Nalbuphine Free Base

The preparation procedure of this oil is the same as that of Injectable oil RH002, except that 100 mg nalbuphine free base is used and the treatment time with the microfluidizer M100-Y is 60 minutes.

4. Injectable Oil RH045 Containing Nalbuphine Free Base

The preparation procedure of this oil was the same as that of Injectable oil RH002, except that 100 mg nalbuphine free base was used and the treatment time with the microfluidizer M100-Y was 30 minutes.

5. Injectable Oil RH048 Containing Nalbuphine Free Base

Into a 1 ml flask 150 mg nalbuphine free base, which is dissolved with pharmasolve™ to a total volume of 1 ml.

6. Injectable Oil RG001 Containing Nalbuphine Free Base

Into a 1 ml flask were added 50 mg nalbuphine free base, 1.8 mg aluminum stearate, and 5 mg chlorobutanol hydrate. Sesame oil pre-heated to 45° C. was then added into the flask to a total volume of 1 ml. After the above ingredients were homogeneously suspended in sesame oil by stirring, the resultant suspension was cooled to room temperature and treated with a mixer (Homomixer, Tokushu Kika, Osaka, Japan), at a rotation rate of 5000 rpm for 60 minutes.

TABLE 1

The formulations of the injectable oil suspensions prepared in Example 2

| | Injectable oil suspension | | | | | |
|---|---|---|---|---|---|---|
| Ingredients | RG001 | RH001 | RH002 | RH044 | RH045 | RH048 |
| Nalbuphine free base | 50 mg | 75 mg | 50 mg | 100 mg | 100 mg | 150 mg |
| Alumimum stearate | 1.8 mg | 2 mg | 2 mg | 2 mg | 2 mg | — |

TABLE 1-continued

The formulations of the injectable oil suspensions prepared in Example 2

| Ingredients | Injectable oil suspension | | | | | |
|---|---|---|---|---|---|---|
| | RG001 | RH001 | RH002 | RH044 | RH045 | RH048 |
| Chlorobutanol hydrate | 5 mg | — | — | — | — | — |
| methyl paraben | — | 1.8 mg | 1.8 mg | 1.8 mg | 1.8 mg | — |
| Propyl paraben | — | 0.2 mg | 0.2 mg | 0.2 mg | 0.2 mg | — |
| Pharmasolve ™ | — | — | — | — | — | q.s. |
| sesame oil | q.s. | q.s. | q.s. | q.s. | q.s. | — |

TABLE 2

The preparative procedures and the physical characteristics of the injectable oil suspensions prepared in Example 2

| Ingredients | Injectable oil suspension | | | | | |
|---|---|---|---|---|---|---|
| | RG001 | RH001 | RH002 | RH044 | RH045 | RH048 |
| Equipment | Homo Mixer | Microfluidizer M110-Y | | | | — |
| Operating pressure or rotational rate | 5000 rpm | 14000 psi | | | | — |
| Treatment Time (minute) | | 60 | | | 30 | — |
| Appearance of product | | Slight yellow suspension | | | | Slight yellow solution |
| Average particle diameter (μm) | 43.95 | 17.54 | 17.27 | 23.74 | 11.37 | — |
| Ratio of particle diameters smaller than 50 μm (%) | 72.37 | 100 | 100 | 88 | 99.32 | — |

The maximal analgesic effects of the injectable oil suspensions of this invention were evaluated through the pharmacokinetic study and in vivo pharmacodynamic study described below. In the examples, the antinociceptive actions of the injectable oil suspensions were tested by the so-called rat cold ethanol tail-flick test established and disclosed by Oliver Yoa-Pu Hu et al. in EP 0615756A1, the disclosure of which is incorporated herein by reference.

EXAMPLE 3

In Vivo Pharmacodynamic Study

Animal

Sprague-Dawley rats (male, 175–225 g) were used. Each group consisted of 6 rats and each rat was injected once intramuscularly on the rear leg.

Materials 25 micromole/2.8 ml of nalbuphine hydrochloride in saline and nalbuphine free base in sesame oil were used as controls. The dose for each rat was 25 μM per kg (nalbuphine hydrochloride and RG001) and 125 μM (RH044, RH045 and RH048), intramuscularly.

Experimental Procedure

A circulating cold ethanol bath was maintained at a temperature of −20° C. After dosing, the rat tail (⅓ from the tip) was immersed into the cold ethanol bath. The latency for the rat to flick its tail from the cold ethanol bath was defined as the nociceptive threshold. The nociceptive effect can be calculated by the following equation:

$$\text{The percentage of nocieptive effect} = \frac{[\text{Latency after dosing}] - [\text{Latency before dosing}]}{[\text{Experimental end}] - [\text{Latency before dosing}]} \times 100\%$$

35, 25, 15 minutes prior to dosing, the male Sprague-Dawley rats were tested to measure the basic response latency. The time to stop the experiment was set at 40 sec. to prevent the tail from cold sores. No cold sores were found in 40 sec. Five minutes after the drug was given to the rat, the flick test was performed at least every 10 minutes.

Results

The detected responses of Sprague-Dawley rats after intramuscular injection with injectable oils RG001 and RH044 prepared as in Example 2 are summarized in Table 3. Nalbuphine was absorbed by Sprague-Dawley rats with $k_{01}$=9.5±9.7 l/h (RG001) or 0.10±0.03 (RH044), which is very similar to that of the traditional dosage form of nalbuphine hydrochloride (12.1±14.1). The elimination half-lives were 21.8±16.9 h (RG001) and 22.4±3.9 (RH044), which are at least 12 times higher than that of the traditional dosage form of nalbuphine hydrochloride (1.9±0.8 h).

The $C_{max}$ and $T_{max}$ values of the injectable oil RG001 were 317±150 ng/ml and 0.68±0.48 h, respectively. The total body clearance of the injectable oil RG001 was 10.5±4.6 ml/h/kg. The relative bioavailability is calculated to be about 34.6%.

On the other hand, The $C_{max}$ and $T_{max}$ values of the injectable oil RH044 were 713±72 ng/ml and 1.3±0.2 h, respectively. The total body clearance of the injectable oil RG001 was 2.5±0.2 ml/h/kg. The relative bioavailability is calculated to be about 34.6%.

Figure 5:
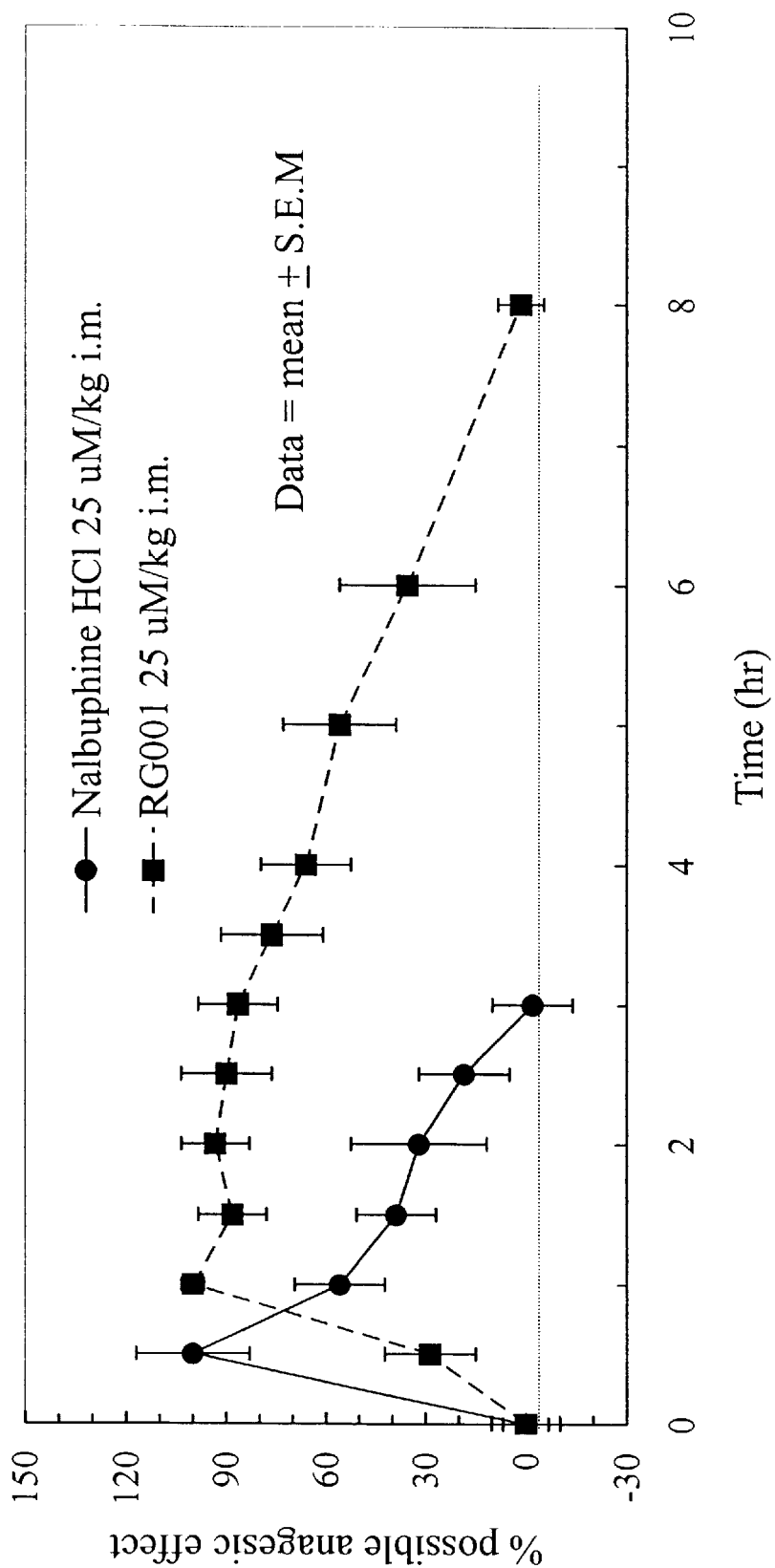
FIG. 5 shows the analgesic effect of nalbuphine on Sprague-Dawley rats after intramuscular injection of the tested preparation (n=6), in which:(●), injection with Nalbuphine HCl at a dose of 25 $\mu$moles/kg; (■), injection with RG001 at a dose of 25 $\mu$M/kg; and "- - -," base line.
Figure 6:
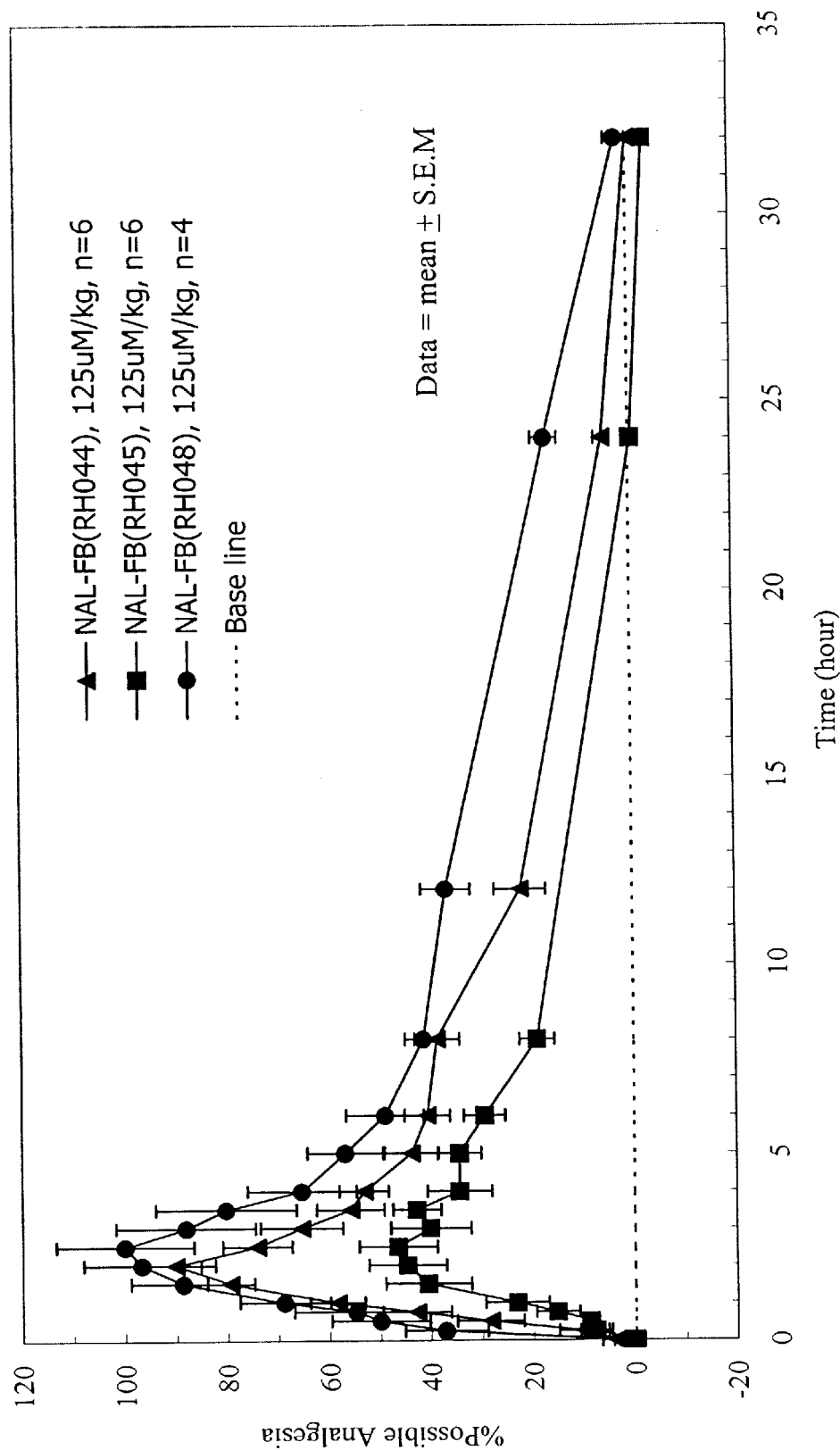
FIG. 6 shows the analgesic effect of nalbuphine on Sprague-Dawley rats as tested with the cold ethanol tail-flick test (n=6), in which: (▼), 125 μmoles/kg of RH044; (■), 125 μmoles/kg of RH045; (●), 125 μmoles/kg of RH048; and "- - -," base line.

The 50% analgesic effects of the intramuscularly injected nalbuphine HCl and RG001 for rats found at 25 μM/kg are 1.2 and 5.3 hours, respectively. The 10% analgesic effect of nalbuphine hydrochloride is 2.7 hours, while that of nalbuphine free base (RG001) is 7.5 hours. (FIG. 5). The 10% analgesic effects of the intramuscular injected RH044, RH045 and RH048 for rats found at 125 μM/kg are 20.2, 15.3 and 27.2 hours, respectively (FIG. 6).

TABLE 3

Pharmacokinetic parameters of nalbuphine in Sprague-Dawley rats after intramuscular injection of nalbuphine-HCl or oil injection dosage form of nalbuphine free base

| Parameters | Nalbuphine-HCl | Injectable oil suspension | |
| --- | --- | --- | --- |
| | | RG001 | RH044 |
| $\alpha$ (1/h) | — | 0.6 ± 0.5 | 0.20 ± 0.06 |
| $\beta$ or $k_{10}$ (1/h) | 0.43 ± 0.21 | 0.06 ± 0.06 | 0.035 ± 0.004 |
| $k_{01}$ (1/h) | 12.1 ± 14.1 | 9.5 ± 9.7 | 0.10 ± 0.03 |
| $t_{1/2}, \alpha$ (h) | — | 2.6 ± 2.4 | 3.8 ± 0.6 |
| $t_{1/2}, \beta$ (h) | 1.9 ± 0.8 | 21.8 ± 16.9 | 22.4 ± 3.9 |
| $t_{1/2}, k_{01}$ (h) | 0.14 ± 0.15 | 0.20 ± 0.22 | 7.1 ± 1.1 |
| Vss/F (l/kg) | 10.5 ± 1.2 | 167.0 ± 52.0 | 58.0 ± 8.3 |
| $C_{max}$ (ng/ml) | 2230 ± 669 | 317 ± 150 | 713 ± 72 |
| $T_{max}$ (h) | 0.45 ± 0.24 | 0.68 ± 0.48 | 1.30 ± 0.20 |
| $AUC^{\infty}$ (h * ng/ml) | 8041 ± 2885 | 2784 ± 1272 | 9733 ± 671 |
| MRT (h) | 3.0 ± 1.2 | 15.9 ± 11.4 | 23.2 ± 3.4 |
| CLt/F (ml/h/kg) | 3.5 ± 0.7 | 10.5 ± 4.6 | 2.5 ± 0.2 |

Data = means ± S.E.

TABLE 4

Pharmacokinetic parameters of nalbuphine in beagles after intramuscular injection of nalbuphine-HCl or oil injection dosage form of nalbuphine free base (n = 5)

| Parameters | Nal-HCl | Injectable oil suspension | |
| --- | --- | --- | --- |
| | | RG001 | RH044 |
| Dose (mg/kg) | 5 | 24 | 24 |
| $\alpha$ (1/h) | 67.9 ± 29.3 | 0.9 ± 0.3 | 0.28 ± 0.06 |
| $\beta$ (1/h) | 0.42 ± 0.15 | 0.08 ± 0.01 | 0.015 ± 0.003 |
| $k_{01}$ (1/h) | 82.5 ± 43.9 | 1.3 ± 0.5 | 0.11 ± 0.02 |
| $t_{1/2}, \alpha$ (h) | 0.13 ± 0.11 | 2.5 ± 1.7 | 3.8 ± 0.9 |
| $t_{1/2}, \beta$ (h) | 2.8 ± 0.9 | 7.7 ± 1.6 | 50.9 ± 8.5 |
| $t_{1/2}, k_{01}$ (h) | 0.12 ± 0.07 | 1.7 ± 1.1 | 7.5 ± 1.4 |
| Vss/F (l/kg) | 32.8 ± 9.0 | 40.8 ± 10.0 | 85.1 ± 14.3 |
| $C_{max}$ (ng/ml) | 2460 ± 755 | 660 ± 88 | 1309 ± 94 |
| $T_{max}$ (h) | 0.09 ± 0.02 | 1.7 ± 0.6 | 2.5 ± 0.5 |
| $AUC^{\infty}$ (h * ng/ml) | 1867 ± 203 | 6373 ± 1169 | 21193 ± 2118 |
| MRT (h) | 2.2 ± 0.5 | 9.1 ± 1.3 | 38.1 ± 6.1 |
| CLt/F (ml/h/kg) | 2.8 ± 0.3 | 4.3 ± 0.7 | 1.2 ± 0.1 |

Data = mean ± S.E.

Figure 7:
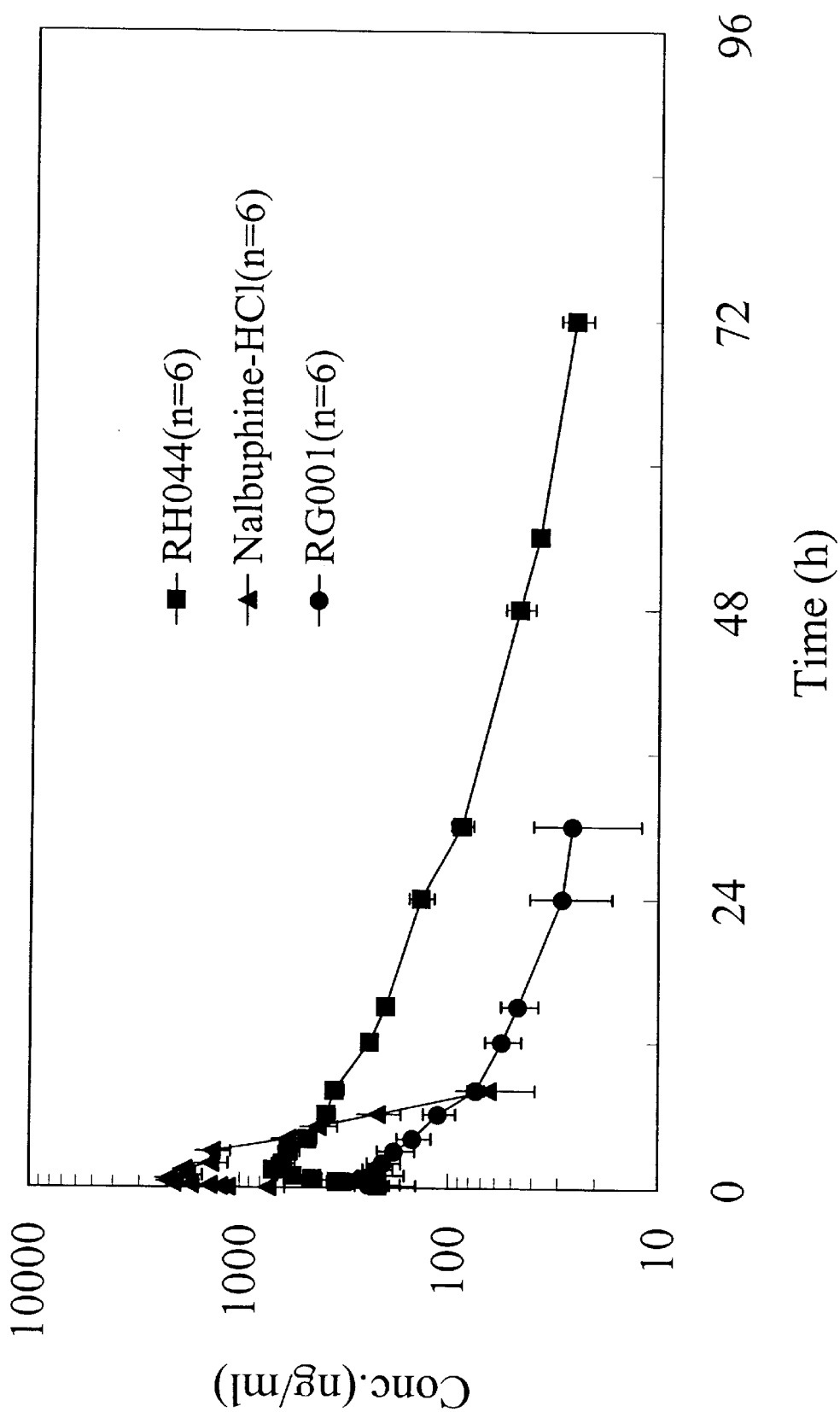
FIG. 7 shows the plasma concentration of nalbuphine in Sprague-Dawley rat plasma after intramuscular injection of the tested preparation (n=6), in which: (●), injection with RG001 at a dose of 24 mg/kg; (■), injection with RH044 at a dose of 24 mg/kg; and (▼), injection with Nalbuphine HCl at a dose of 24 mg/kg.

The pharmacokinetic properties of nalbuphine in Sprague-Dawley rats after intramuscular injection with traditional dosage form of nalbuphine hydrochloride and the present injectable oils containing nalbuphine free base were summarized in FIG. 7 and Table 3.

Nalbuphine was quickly absorbed by Sprague-Dawley rats with $k_{01}$ 12.1±14.1 l/h. The elimination half-life was 1.9±0.8 h. $C_{max}$ and $T_{max}$ were 2230±669 ng/ml and 0.45±0.24 h, respectively. The total body clearance was 3.5±0.7 ml/h/kg.

Plasma concentration of nalbuphine was also determined in beagles after injection with the oil suspension and control compositions.

Figure 8:
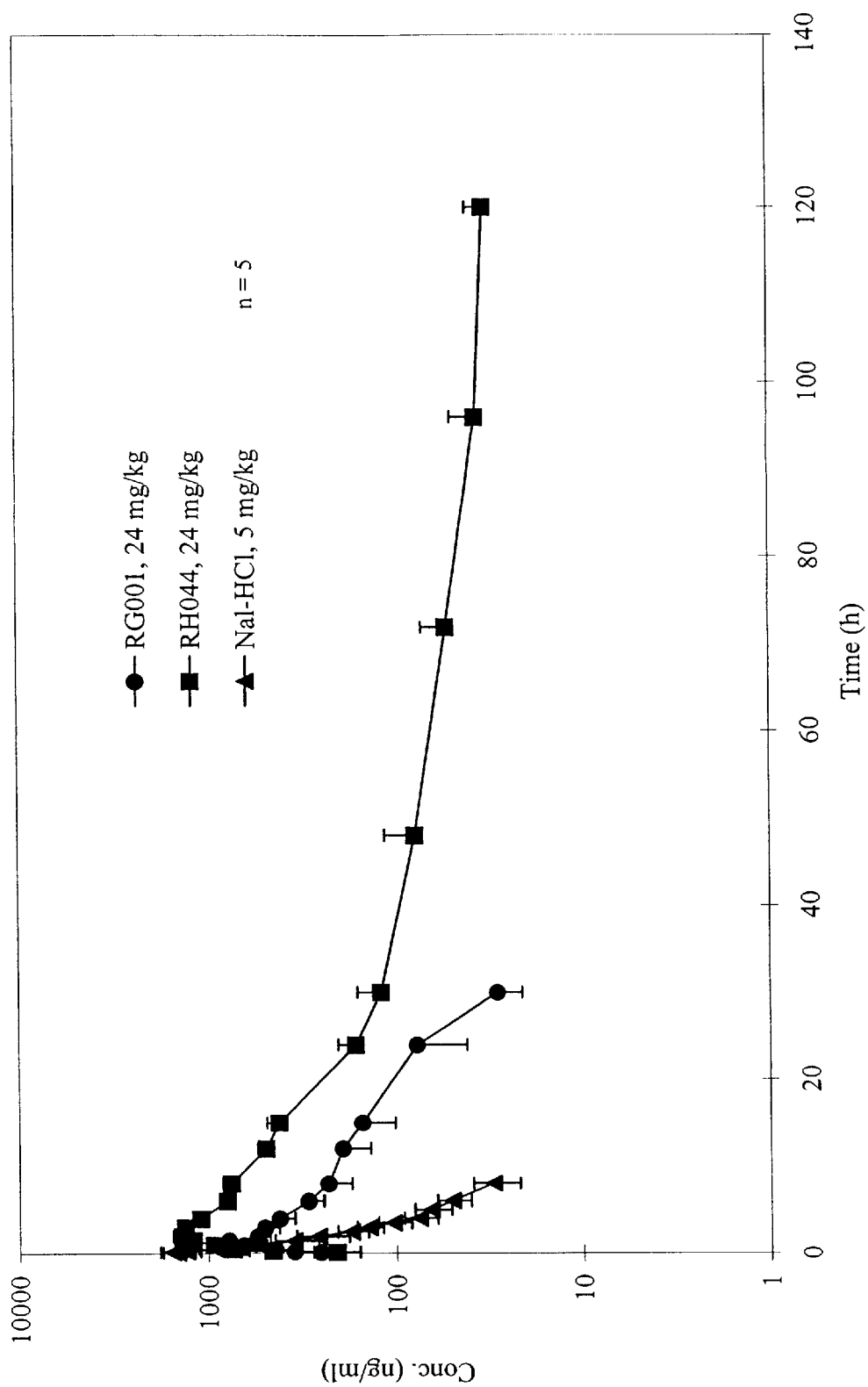
FIG. 8 shows the plasma concentration of nalbuphine in beagle's plasma after intramuscular injection of the tested preparation (n=5), in which:(●), injection with RG001 at a dose of 24 mg,/kg; (■), injection with RH044 at a dose of 24 mg/kg; and (▼), injection with nalbuphine HCl at a dose of 5 mg/kg.

The pharmacokinetic properties of nalbuphine in beagles after intramuscular injection with traditional nalbuphine hydrochloride and nalbuphine free base oil suspensions are shown in FIG. 8 and Table 4. Nalbuphine HCl was quickly absorbed by beagles with $k_{01}$ 82.5±43.9 l/h. The elimination half-life was 2.8±0.9 h. $C_{max}$ and $T_{max}$ were 2460±755 ng/ml and 0.09±0.04 h, respectively. Total body clearance was 2.8±0.3 ml/h/kg.

The pharmacokinetic properties of nalbuphine of beagles after intramuscular injected with long-acting dosage form RG001 and RH044 of nalbuphine free base are shown in Table 4. The oil suspensions of nalbuphine were absorbed by beagles with $k_{01}$ values of 1.3±0.5 l/h (RG001) and 0.11±0.02 l/h (RH044) significantly less than the $k_{01}$ value of the traditional nalbuphine hydrochloride preparation (82.5 l/h). The elimination half-lives of the two oil suspensions were 7.7±1.6 h (RG001), and 50.9±8.5 (RH044), 3–20 times longer than that for the traditional nalbuphine hydrochloride. $C_{max}$ and $T_{max}$ of dosage RG001 were 660±88 ng/ml and 1.7±0.6 h, respectively. Total body clearance of dosage RG001 was 4.3±0.7 ml/h/kg. On the other hand, $C_{max}$ and $T_{max}$ of dosage RH044 were 1309±94 ng/ml and 2.5±0.5 h, respectively. Total body clearance of dosage RH044 was 1.2±0.1 ml/h/kg.

Nalbuphine was absorbed very quickly by beagles intramuscularly injected with long-acting dosage form of RG001, RH044 and traditional nalbuphine hydrochloride. Both long-acting dosage form of RG001 and RH044 produced lower $C_{max}$ for nalbuphine, reducing the possibility of side effects, and had longer elimination half-lives, thus prolonging the duration of pharmacological activity compared to the traditional formulation of nalbuphine hydrochloride. Nalbuphine from the sustained-released dosage form of RG001 and RH044 were maintained higher than 10 ng/ml, the clinical therapeutic concentration, over 2 days.

Nalbuphine was absorbed very quickly by beagles intramuscularly injected with long-acting dosage form of YP8000 and traditional nalbuphine hydrochloride. Long-acting dosage form of YP8000 produced lower $C_{max}$ of nalbuphine, thereby reducing the possibility of undesirable side effects, and exhibited a longer elimination half-life to prolong the drug activity compared to the traditional formulation of nalbuphine hydrochloride. Due to the extension of elimination half-life the clinical therapeutic effect lasts 3–12 times longer than that of the traditional formulation.

The present injectable oil preparations of nalbuphine thus exhibit two very advantageous features: providing long-acting analgesia while greatly reducing the possibility of addiction and respiratory inhibition.

While the invention has been described with reference to the above specific embodiments, it is apparent that numerous modifications and variations can be made without departing from the scope and spirit of this invention. It is therefore intended that this invention be determined by the descriptions stated herein and the appended claims.

What is claimed is:

1. A controlled-release pharmaceutical preparation comprising a pharmaceutical composition which is an oil suspension comprising an analgesic which is a free base of nalbuphine or a pharmaceutically acceptable salt of nalbuphine;

an injectable oil, wherein said injectable oil is in admixture with said free base of nalbuphine or said pharmaceutically acceptable salt of nalbuphine to form microparticles less than 100 μm in size; and optionally a pharmaceutically acceptable excipient.

2. The controlled-release pharmaceutical preparation according to claim 1, wherein said pharmaceutically acceptable salt of nalbuphine is nalbuphine HCl.

3. The controlled-release pharmaceutical preparation according to claim 1, wherein said microparticles are less than 50 μm in size.

4. The controlled-release pharmaceutical preparation according to claim 1, wherein said injectable oil is selected from the group consisting of sesame oil, ethyl ester of peanut oil, soybean oil, and combinations thereof.

5. The controlled-release pharmaceutical preparation according to claim 1, wherein the injectable oil is sesame oil.

6. The controlled-release pharmaceutical preparation according to claim 1, wherein said pharmaceutically acceptable excipient is at least one selected from the group consisting of aluminum stearate, chlorobutanol hydrate, methyl paraben, propyl paraben, and combinations thereof.

7. The controlled-release pharmaceutical preparation according to claim 1, wherein said microparticles are prepared by mixing the analgesic and the injectable oil in an ultra high energy mixing equipment.

8. The controlled-release pharmaceutical preparation according to claim 7, wherein said ultra high energy mixing equipment is operated for 10 to 75 minutes.

9. The controlled-release pharmaceutical preparation according to claim 1, wherein the preparation is administered via an intramuscular, subcutaneous, intracerebroventricular or percutaneous route, or for direct injection into the spinal marrow.

10. The controlled-release pharmaceutical preparation according to claim 1, wherein the preparation is administered via an intramuscular route.

11. A process for preparing the controlled-release pharmaceutical preparation according to claim 1 comprising the steps of:

mixing the analgesic with the injectable oil to form the oil suspension, and treating the oil suspension with an ultra high energy mixing equipment, to form microparticles with a particle size less than 100 μm.

12. The process according to claim 11, wherein said injectable oil is pre-heated to about 45° C. before mixing with the analgesic.

13. The process according to claim 11, wherein the injectable oil is an oil selected from the group consisting of sesame oil, ethyl ester of peanut oil, soybean oil, and combinations thereof.

14. The process according to claim 9, further comprising admixing a pharmaceutically acceptable excipient with the analgesic prior to the addition of the injectable oil.

15. The process according to claim 14, wherein the pharmaceutically acceptable excipient is at least one selected from the group consisting of aluminum stearate, chlorobutanol hydrate, methyl paraben, and propyl paraben.

16. The controlled-release pharmaceutical preparation according to claim 7 wherein said ultra high energy equipment is a high pressure homogenizer, and wherein said high pressure homogenizer is under a pressure of 10,000 to 30,000 psi.

17. The controlled-release pharmaceutical preparation according to claim 16, wherein said high pressure homogenizer is under a pressure of about 14,000 psi.

18. The process according to claim 11, wherein said ultra high energy mixing equipment is a high pressure homogenizer, and wherein said high pressure homogenizer is under a pressure of 10,000 to 30,000 psi.

19. The controlled-release pharmaceutical preparation according to claim 18, wherein said high pressure homogenizer is under a pressure of about 14,000 psi.

* * * * *